(12) United States Patent
Philippe et al.

(10) Patent No.: US 7,078,047 B2
(45) Date of Patent: *Jul. 18, 2006

(54) COSMETIC OR PHARMACEUTICAL COMPOSITIONS COMPRISING HOMOPOLYMERS AND SALTS THEREOF

(75) Inventors: Michel Philippe, Wissous (FR); Sylvie Benard, Attainville (FR); Christian Blaise, Saint Mande (FR)

(73) Assignee: L'Oreal S.A., Paris (FR)

( * ) Notice: Subject to any disclaimer, the term of this patent is extended or adjusted under 35 U.S.C. 154(b) by 410 days.

This patent is subject to a terminal disclaimer.

(21) Appl. No.: 10/086,248

(22) Filed: Mar. 4, 2002

(65) Prior Publication Data
US 2002/0172654 A1 Nov. 21, 2002

(30) Foreign Application Priority Data
Mar. 5, 2001 (FR) .................................. 01 02980

(51) Int. Cl.
*A61K 6/00* (2006.01)
*A01N 43/16* (2006.01)
*A01N 33/08* (2006.01)

(52) U.S. Cl. ...................... 424/401; 514/460; 514/665; 514/666

(58) Field of Classification Search ................. 424/61, 424/401, 65, 63; 514/184, 460, 665, 666
See application file for complete search history.

(56) References Cited

U.S. PATENT DOCUMENTS

| 4,147,782 | A |   | 4/1979 | Klein et al. |
| 4,600,526 | A |   | 7/1986 | Gallot et al. |
| 5,629,282 | A |   | 5/1997 | Bhakoo |
| 6,585,962 | B1 | * | 7/2003 | Philippe et al. ................ 424/61 |

FOREIGN PATENT DOCUMENTS

| DE | 37 24 460 | 2/1988 |
| EP | 0 928 608 | 7/1999 |
| EP | 0 958 811 | 11/1999 |
| EP | 0 959 092 | 11/1999 |
| FR | 2 533 209 | 3/1984 |
| FR | 2 776 510 | 10/1999 |
| GB | 2 217 319 | 10/1989 |
| WO | WO 99/37279 | 7/1999 |

OTHER PUBLICATIONS

Co-pending Application-Title: Anti-Wrinkle Cosmetic or Pharmaceutical Compositions Comprising Polymers and Salts Thereof Inventor(s): Michel Philippe et al. U.S. Filing Date: Mar. 4, 2002.
Jean Morrelle, "Lipoaminoacides et Cosmétologie," Parfums Cosmetiques Savons de France, Paris, vol. 3, No. 1, Feb. 1, 1973, pp. 82-93.
Bernard Gallot et al., "Liquid Crystalline Phases and Emulsifying Properties of Block Copolymer Hydrophobic Aliphatic and Hydrophilic Peptidic Chains," ACS Symposium Series, Washington, D.C., No. 384, 1989, pp. 116-128.
L. Rasseneur et al., "Influence des Différents Constituants de la Couche Cornee sur la Mesure de son Élasticité," International Journal of Cosmetic Science, vol. 4, No. 6, Dec. 1982, pp. 247-260.
Database WPI, Section CH, Week 200020, Derwent Publications Ltd., London, GB;,AN 2000-232901, XP002188278.
Patent Abstracts of Japan, vol. 016, No. 528, Oct. 29, 1992, JP 04 198114 A.
Patent Abstracts of Japan, vol. 013, No. 260, Jun. 15, 1989, JP 01 061412 A.
Patent Abstracts of Japan, vol. 1995, No. 11, Dec. 26, 1995, JP 07 223920 A.
English language abstract of DE 37 24 460, Feb. 4, 1988.
English language abstract of EP 0 958 811, Nov. 24, 1999.
English language abstract of EP 0 959 092, Nov. 24, 1999.
English language Derwent Abstract of FR 2 776 510, Oct. 1, 1999.

* cited by examiner

*Primary Examiner*—Shengjun Wang
*Assistant Examiner*—Yong S. Chong
(74) *Attorney, Agent, or Firm*—Finnegan, Henderson, Farabow, Garrett & Dunner, L.L.P.

(57) ABSTRACT

Use of at least one material chosen from homopolymers and salts thereof of formula (I), defined herein, for moisturizing the skin, mucous membranes and/or keratin fibres, and/or as a moisturizer and/or emollient, for the skin, mucous membranes and/or keratin fibres. The invention also relates to a cosmetic or pharmaceutical composition for moisturizing the skin, mucous membranes and/or keratin fibres, comprising at least one material chosen from homopolymers and salts thereof of formula (I).

5 Claims, No Drawings

COSMETIC OR PHARMACEUTICAL COMPOSITIONS COMPRISING HOMOPOLYMERS AND SALTS THEREOF

The present invention relates to the use of at least one material chosen from homopolymers and salts thereof of formula (I), as defined herein, which can be referred to as polyamino acid derivatives, in a composition, such as a cosmetic or pharmaceutical composition, intended to be applied to the skin or mucous membranes, in order, for example, to improve their moisturization or to prevent them from drying out.

Various classes of polyamino acids referenced in the literature are known, for their numerous uses, especially in cosmetics.

Thus, Japanese patent application JP-07/041 467 relates to a class of high molecular weight polyamino acids consisting essentially of cysteine.

Japanese patent application JP-06/248 072 relates to a class of polyamino acids characterized by the presence of thiol and/or disulphide functions; these polyamino acids react with the thiol linkages of keratin, thus forming disulphide bridges, thereby enabling the sheen and coloration properties of the hair to be enhanced.

French patent application FR-2 533 209 relates to amphipathic lipopeptides consisting of a hydrophilic peptide chain and a hydrophobic chain of 8 to 24 carbon atoms, and also to their use as emulsifiers of immiscible media or for the production of liquid crystals.

Patent application FR 2 776 510 relates to cosmetic compositions intended for reinforcing or caring for keratin fibres, especially hair fibres, which comprise polyamino acid derivatives.

Polyamino acids consisting essentially of neutral-chain and acidic-chain amino acids have been referenced in Japanese patent application JP-04/198 114, and are used in general as moisturizers. The compounds described in the said patent application are copolymers of an acidic-chain amino acid with a neutral-chain amino acid. The copolymerization requires a preactivation of each of the amino acids; moreover, it is also necessary to protect the acid function of the acidic-chain amino acid before the activation step. These two steps of protection and activation can make the synthetic process particularly complex and economically and industrially unviable.

The present invention provides a novel class of homopolymers and salts thereof that can be referred to as polyamino acid derivatives that can overcome at least one of the drawbacks of the prior art, that may be obtained by a simple and industrial process, and that can have moisturizing properties.

One subject of the invention is thus the use of at least one material chosen from homopolymers and salts thereof of formula (I) as defined below, for moisturizing the skin, mucous membranes and/or keratin fibres, and/or the use of said at least one material on the skin, mucous membranes and/or keratin fibres in order to improve their moisturization and/or to prevent them from drying out.

A subject of the invention is also the use of at least one material chosen from homopolymers and salts thereof of formula (I) as defined below, as a moisturizer and/or emollient, especially for the skin, mucous membranes and/or keratin fibres.

Another subject of the invention is a cosmetic or pharmaceutical composition for improving the moisturization of the skin, mucous membranes and/or keratin fibres, comprising at least one material chosen from homopolymers and salts thereof of formula (I) as defined below.

Another subject of the invention is a method of improving moisturizing of and/or preventing from drying out a substance chosen from skin, mucous membranes and keratin fibres, comprising applying to said substance at least one material chosen from homopolymers and salts thereof of formula (I), as defined below.

Another subject of the invention is a moisturizer and/or emollient for a substance chosen from skin, mucous membranes and keratin fibres, comprising at least one material chosen from homopolymers and salts thereof of formula (I).

Another subject of the invention is a method for improving the moisturizing of and/or preventing from drying out a substance chosen from skin, mucous membranes and keratin fibres, comprising, applying to the substance, products chosen from make-up products for caring for, treating, cleansing and protecting the skin of the face and the body including the scalp, haircare compositions, antisun compositions, artificial tanning compositions. and after-sun care compositions, the products/compositions comprising at least one material chosen from homopolymers and salts thereof of formula (I), as defined below.

Another subject of the invention is a method for the cosmetic treatment of a substance chosen from skin, mucous membranes and keratin fibres, comprising applying to the substance, at least one material chosen from homopolymers and salts thereof of formula (I), as defined below It has been found that the compounds according to the invention can have very good moisturizing power on the skin, mucous membranes and keratin fibres (such as hair, eyelashes, eyebrows and nails). They may be used advantageously when an effect of combating the drying of the skin and/or the hair is desired in cosmetics or in pharmaceuticals.

These compounds can have the advantage of improving and/or restoring the barrier function when they are applied to the skin.

They can have emollient and softening properties, especially on the skin and the hair. They may also be readily dissolved in the fatty phases of cosmetic or pharmaceutical compositions.

The compounds according to the invention may be used for treating damaged and/or aged skin, and also damaged hair or nails, in the cosmetic or pharmaceutical field.

Moreover, the synthesis of these compounds can be very fast and readily industrializable.

The at least one material used in the present invention is chosen from homopolymers and salts thereof corresponding to formula (I):

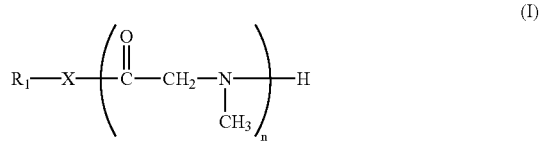

in which:

X is chosen from —O—, —S— and —NR, wherein R is chosen from hydrogen and linear and branched, saturated and unsaturated $C_1$–$C_6$ hydrocarbon-based radicals, $R_1$ is chosen from:

(i) hydrogen, (ii) linear and branched, saturated and unsaturated $C_1$–$C_{40}$ hydrocarbon-based radicals, optionally substituted with at least one group chosen from hydroxyl and —NR'R",
in which R' and R" are chosen from, independently of
each other, hydrogen and linear and branched, saturated
and unsaturated $C_1$–$C_6$ hydrocarbon-based radicals;

wherein the $C_1$–$C_{40}$ hydrocarbon-based radicals can be interrupted with at least one hetero atom chosen from N, O and Si, (iii) a radical chosen from

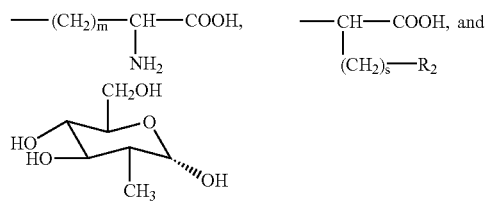

in which:

m is 1, 2, 3, 4 or 5;

s is an integer between 0 and 4 inclusive;

$R_2$ is chosen from hydrogen, —$NH_2$, —OH, —SH, —$CHOHCH_3$, —$CONH_2$,

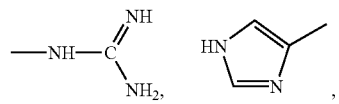

—$C_6H_5$ and —$C_6H_5pOH$, n is an average number of repeating units of greater than 1 such that the weight average molecular weight of the at least one material is between 200 and 200 000 inclusive.

The at least one material may also be chosen from salts, such as mineral and organic salts that are compatible with use in cosmetics and pharmaceuticals.

In one embodiment, X is —NR where R is chosen from hydrogen and linear and branched, saturated $C_1$–$C_4$ hydrocarbon-based radicals, such as methyl and ethyl radicals.

In one embodiment, $R_1$ is chosen from linear and branched, saturated and unsaturated, $C_1$–$C_{22}$, such as $C_4$–$C_{20}$, hydrocarbon-based radicals, optionally substituted with at least one hydroxyl, such as with two, three, four or five —OH groups, and radicals chosen from:

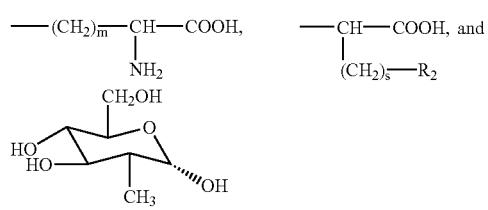

in which:

m is 1, 2, 3, 4 or 5;

s is an integer between 1 and 3 inclusive

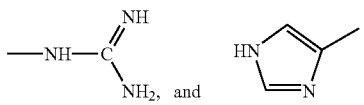

In one embodiment, $R_2$ is chosen from —$CONH_2$,

In another embodiment, $R_1$ is chosen from one of the following formulae:

$C_{15}H_{31}$—CH(OH)—CH($CH_2$OH)—
$C_{10}H_{21}$—CH($C_8H_{17}$)—$CH_2$—
$C_{16}H_{33}$—
$C_8H_{17}$—CH=CH—$C_8H_{16}$—

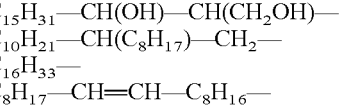

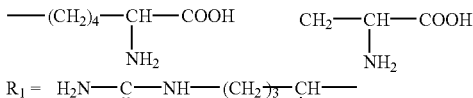

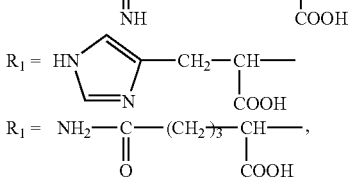

$CH_2(OH)$—$CH(OH)$—$CH(OH)$—$CH(OH)$—$CH(OH)$—$CH_2$—, and

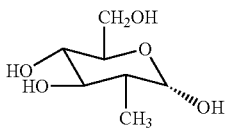

In one embodiment, n is between 3 to 500 inclusive, and/or is such that the weight average molecular weight of the at least one material is between 300 and 50 000, inclusive.

The at least one material chosen from homopolymers and salts thereof of formula (I) may be obtained by processes that are well-known to those skilled in the art, such as a polycondensation reaction between at least one N-carboxyanhydride of formula:

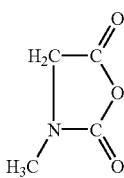

and a nucleophilic compound of formula $R_1$—XH in which $R_1$ and X have the same meanings as those given above for formula (I).

This process is described in French patent application FR 2 776 510, the disclosure of which is specifically incorporated by reference herein.

The at least one material may be used, alone or as a mixture, in an amount of from 0.001% to 30% by weight relative to the total weight of the composition, such as an amount of from 0.01% to 15% by weight relative to the total weight of the composition.

The at least one material according to the invention may accommodate various uses, such as in cosmetic or pharmaceutical compositions, which then comprise a physiologically acceptable medium, such as cosmetically and pharmaceutically acceptable media.

This medium, its constituents, their amount, the presentation form of the composition and the method for preparing it may be chosen by a person skilled in the art on the basis of his general knowledge, depending on the desired type of composition.

In general, this medium may be anhydrous or aqueous.

When the composition comprises an aqueous phase, the said phase may comprise water, a floral water and/or a mineral water.

The said phase may also comprise alcohols such as $C_1$–$C_6$ monoalcohols and/or polyols, such as glycerol, butylene glycol, isoprene glycol, propylene glycol and polyethylene glycol.

The composition may also comprise a fatty phase, which may comprise fatty substances that are liquid at 25° C., such as volatile and non-volatile oils of animal, plant, mineral and synthetic origin; fatty substances that are solid at 25° C. such as waxes of animal, plant, mineral and synthetic origin; pasty fatty substances; gums; mixtures thereof.

The volatile oils are generally oils having, at 25° C., a saturating vapour pressure at least equal to 0.5 millibar (i.e. 50 Pa). Among the constituents of the fatty phase that may be mentioned are:

cyclic volatile silicones containing from 3 to 8, such as from 4 to 6, silicon atoms;

cyclocopolymers such as dimethylsiloxane/methylalkylsiloxane;

linear volatile silicones comprising from 2 to 9 silicon atoms;

hydrocarbon-based volatile oils, such as isoparaffins, isododecane and fluoro oils;

poly($C_1$–$C_{20}$)alkylsiloxanes, such as those comprising trimethylsilyl end groups, for example, linear polydimethylsiloxanes and alkylmethylpolysiloxanes such as cetyl dimethicone (CTFA name);

silicones modified with at least one group chosen from fluorinated and non-fluorinated aliphatic and aromatic groups, and functional groups, such as hydroxyl, thiol and amine groups;

phenylsilicone oils;

oils of animal, plant and mineral origin, such as animal and plant oils formed from fatty acid esters of polyols, for example, liquid triglycerides, such as sunflower oil, corn oil, soybean oil, marrow oil, grapeseed oil, sesame oil, hazelnut oil, apricot oil, almond oil and avocado oil; fish oils, glyceryl tricaprocaprylate, and plant and animal oils of formula $R_1COOR_2$, in which $R_1$ is chosen from higher fatty acid residues containing from 7 to 19 carbon atoms and $R_2$ is chosen from branched hydrocarbon-based chains containing from 3 to 20 carbon atoms, for example purcellin oil; liquid paraffin, liquid petroleum jelly, perhydrosqualene, wheat germ oil, beauty-leaf oil, sesame oil, macadamia oil, grapeseed oil, rapeseed oil, coconut oil, groundnut oil, palm oil, castor oil, jojoba oil, olive oil, and cereal germ oil; fatty acid esters; alcohols; acetylglycerides; octanoates, decanoates and ricinoleates of alcohols and of polyalcohols; fatty acid triglycerides; glycerides;

fluoro oils and perfluoro oils;

silicone gums;

waxes of animal, plant, mineral and synthetic origin, such as microcrystalline waxes, paraffin, petrolatum, petroleum jelly, ozokerite and montan waxes; beeswax, lanolin and its derivatives; candelilla wax, ouricury wax, carnauba wax, Japan wax, cocoa butter, cork fibre wax and sugar cane wax; hydrogenated oils that are solid at 25° C., ozokerites, fatty esters and glycerides that are solid at 25° C.; polyethylene waxes and the waxes obtained by Fischer-Tropsch synthesis; hydrogenated oils that are solid at 25° C.; lanolins; fatty esters that are solid at 25° C.; silicone waxes; and fluoro waxes.

The composition may also comprise any additive usually used in the envisaged field of application, such as surfactants, antioxidants, fragrances, essential oils, preserving agents, cosmetic and pharmaceutical active agents, vitamins, essential fatty acids, sphingolipids, self-tanning agents, sunscreens, film-forming polymers, thickeners, colorants, pigments, fillers and nacres.

A person skilled in the art can take care to select the optional additional compounds and the amount thereof, such that the advantageous properties of the composition according to the invention are not, or are not substantially, adversely affected by the envisaged addition.

The compositions according to the invention can, for example, be applied to the skin of the face and the body, to mucous membranes and/or to keratin fibres such as the nails, the eyelashes and the hair.

The compositions according to the invention may be in any conceivable presentation form, such as oily and aqueous solutions; oily and aqueous gels; oil-in-water, water-in-oil and multiple emulsions; dispersions of oil in water and of water in oil; and multi-phase systems, such as two-phase systems.

These compositions may be:

in a form chosen from make-up products for facial skin, body skin, the lips and keratin fibres (such as nails, eyelashes, eyebrows and hair), such as foundations, tinted creams, face powders, eye shadows, free and compact powders, concealer sticks, cover sticks, mascara, lipsticks and nail varnishes;

products for caring for, treating, cleansing and protecting the skin of the face and the body including the scalp, such as facial and body care compositions (day, night, and moisturizing compositions); anti-wrinkle and anti-ageing compositions for the face; matt-effect compositions for the face; compositions for irritated skin; make-up-removing compositions; body milks, especially moisturizing and optionally after-sun body milks;

haircare compositions, such as haircare creams and gels, and moisturizing products;

antisun compositions, artificial tanning (self-tanning) compositions and after-sun care compositions.

The invention is illustrated in greater detail in the examples which follow.

EXAMPLE 1

Preparation of the compound of formula (I) in which:
$R_1$=$CH_2(OH)$—$CH(OH)$—$CH(OH)$—$CH(OH)$—$CH(OH)$—$CH_2$—, X=—NH— and n=12 (theoretical index)

10 g (0.08 mol) of sarcosine N-carboxyanhydride are introduced into a 500 ml conical flask with stirring, followed by addition of 100 ml of distilled water (pH 6.7) and addition of 0.006 mol of glucamine in a single portion.

A considerable evolution of $CO_2$ takes place, after which stirring of the mixture is continued for about 30 minutes at 25° C.

After evaporating off the water under reduced pressure and drying under vacuum, a light-beige powder is obtained.

EXAMPLE 2

Preparation of the compound of formula (I) in which:
$R_1$=CH$_2$(OH)—CH(OH)—CH(OH)—CH(OH)—CH(OH)—CH$_2$—, X=—NCH$_3$— and n=12 (theoretical index)

This compound is prepared according to the same procedure as that described in Example 1, replacing the glucamine with the corresponding molar amount of N-methylglucamine.

EXAMPLE 3

Preparation of the compound of formula (I) in which:

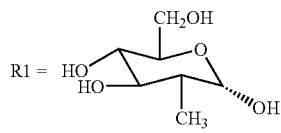

X=—NH— and n=12 (theoretical index)

This compound is prepared according to the same procedure as that described in Example 1, replacing the glucamine with the corresponding molar amount of pre-desalified glucosamine.

EXAMPLE 4

Day Cream

A moisturizing facial care cream is prepared, comprising:

| | |
|---|---|
| cetyl alcohol | 2.5 g |
| sorbitan tristearate | 0.9 g |
| PEG-40 stearate | 2 g |
| glyceryl stearate | 3 g |
| myristyl myristate | 2 g |
| hydrogenated polyisobutene | 2.5 g |
| octyl palmitate | 4 g |
| polydimethylsiloxane (10 cm$^2$.s) | 5 g |
| apricot kernel oil | 5.7 g |
| compound of Example 2 | 0.5 g |
| preserving agents, fragrance | qs |
| water | qs 100 g |

A day cream is obtained that is in the form of an emulsion allowing the skin to be satisfactorily covered and protected; this cream is suitable for normal and dry skin.

EXAMPLE 5

Night Cream

A moisturizing facial care cream is prepared, comprising:

| | |
|---|---|
| mixture of glyceryl mono- and distearate and of POE stearate | 2 g |
| apricot kernel oil | 17 g |
| cyclopentadimethylsiloxane | 1.5 g |
| carbomer | 0.75 g |
| triethanolamine | 0.75 g |
| compound of Example 1 | 3 g |
| preserving agents | qs |
| water | qs 100 g |

A night cream is obtained that is in the form of a thickened, shiny emulsion that is soft to apply. The cream nourishes and hydrates the skin and is suitable for dry skin.

EXAMPLE 6

Measurement of the Moisturization

The moisturization provided by three compounds according to the invention was measured in vitro by measuring the elastic modulus of the stratum corneum, using a device of the dermometer type. This device was described by L. Rasseneur et al. in Influence des Différents Constituants de la Couche Cornée sur la Mesure de son Elasticité [Influence of the Various Constituents of the Horny Layer on the Measurement of its Elasticity], *International Journal of Cosmetic Science*, 4, 247–260 (1982).

The principle comprises measuring, before treatment, the elastic modulus of the stratum corneum at the start of the creep threshold, which is characteristic of viscoelastic materials. The elastic modulus after treatment is then determined at the same elongation of the stratum corneum.

It is moreover known that the elastic modulus reduces greatly when the water content, and thus the moisturization, increases.

The reduction index of the modulus characterizes the moisturizing effect of the treatment:

$$100 \times (E_{treated} - E_{control})/E_{control}$$

This test was performed in vitro on isolated stratum corneum to which was applied a solution at a concentration of 3% by weight in water of the test compound.

To prepare these compositions, the compounds are dissolved in hot (60° C.) DMF, to a concentration of 3% by weight; the solution is maintained at 60° C. until completely dissolved. It is cooled to 30° C. before use.

Test samples of 0.6×0.4 cm of stratum corneum with a thickness of between 10 and 20 microns are used, mounted on the MTT 610 extensiometer sold by the company Diastron, and placed between the jaws of the dermometer.

The test sample is placed between two jaws and then left for 12 hours in an atmosphere at 30° C. and 75% relative humidity. These jaws are then attached to the dermometer.

The test sample is pulled at a speed of 1 mm/minute by a length of between 5% and 10% of the initial length to determine the length $L_0$ at and above which the test sample begins to exert a force on the jaws that is detected by the device.

The test sample is then relaxed, after which 2 mg of the test solution are applied over the entire surface of the stratum corneum. After total evaporation (drying at room temperature for 30 minutes), the test sample is pulled under the same conditions as those described above so as to determine also the length $L_1$ for the treated test sample.

The percentage of retraction is determined by the ratio:

$$100 \times (L_1 - L_0)/L_0$$

To characterize a tensioning effect, this percentage must be negative, and the tensioning effect is proportionately greater the larger the absolute value of the percentage of retraction.

Measurements are carried out at times $T_0$, $T_1$, $T_2$ and $T_4$, that is to say just before the treatment, and 2 hours, 4 hours, 6 hours and 20 hours after applying the test compound.

The following results are obtained (average on 5 samples):

% Variation in the elastic modulus of the sample of stratum corneum:

|  | After 2 hours | After 4 hours | After 6 hours | After 20 hours |
|---|---|---|---|---|
| Aqueous 3% solution of the compound of Example 1 | −21% | −29% | −34% | −38% |
| Aqueous 3% solution of the compound of Example 2 | −29% | −38% | −45% | −49% |
| Aqueous 3% solution of the compound of Example 3 | −31% | −32% | −28% | −42% |
| Water | +1% | −1% | 0 | −2% |

These results show a strong moisturizing activity with a very remarkable feature as regards the expression of the activity, since the said activity increases over time (increase between the results at 2 hours and at 20 hours).

What is claimed is:

1. A method of improving the moisturizing of and/or preventing from drying out a substance chosen from skin and mucous membranes, comprising:

applying to the substance, at least one material chosen from homopolymers and salts thereof of formula (I):

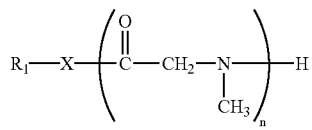

(I)

in which:

X is chosen from —O—, —S— and —NR, wherein R is chosen from hydrogen and linear and branched, saturated and unsaturated $C_{1-C6}$ hydrocarbon-based radicals, $R_1$ is

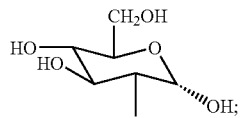

and n is an average number of repeating units of greater than 1 such that the weight average molecular weight of the at least one material is between 200 and 200,000, inclusive.

2. A method for improving the moisturizing of and/or preventing from drying out a substance chosen from skin and mucous membranes, comprising, applying to the substance, a composition chosen from make-up products for caring for, treating, cleansing and protecting the skin of the face and the body, haircare compositions, antisun compositions, artificial tanning compositions and after-sun care compositions, thecomposition comprising at least one material chosen from homopolymers and salts thereof of formula (I):

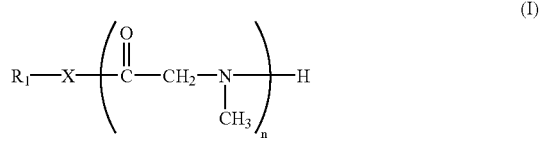

(I)

in which:

X is chosen from —O—, —S— and —NR, wherein R is chosen from hydrogen and linear and branched, saturated and unsaturated $C_{1-C6}$ hydrocarbon-based radicals, $R_1$ is

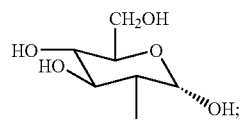

and n is an average number of repeating units of greater than 1 such that the weight average molecular weight of the at least one material is between 200 and 200,000, inclusive.

3. The method of claim 2, wherein said skin comprises facial skin, body skin and the lips and wherein said body skin comprises scalp.

4. A method for the cosmetic treatment of a substance chosen from skin and mucous membranes, comprising:

applying to the substance a moisturizer and/or emollient comprising at least one material chosen from homopolymers and salts thereof of formula (I):

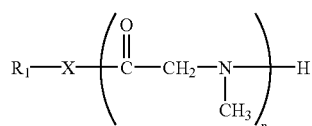

(I)

in which:

X is chosen from —O—, —S— and —NR, wherein R is chosen from hydrogen and linear and branched, saturated and unsaturated $C_{1-C6}$ hydrocarbon-based radicals, $R_1$ is

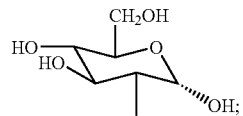

and n is an average number of repeating units of greater than 1 and such that the weight average molecular weight of the at least one material is between 200 and 200,000, inclusive.

5. The method of claim 4, wherein the cosmetic treatment comprises cosmetic care of at least one substance chosen from damaged skin, aged skin, damaged hair, aged hair, damaged nails, and aged nails.

* * * * *